US007994188B2

(12) United States Patent
Disse

(10) Patent No.: US 7,994,188 B2
(45) Date of Patent: Aug. 9, 2011

(54) COMPOUNDS FOR TREATING INFLAMMATORY DISEASES

(75) Inventor: Bernd Disse, Mainz (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 0 days.

(21) Appl. No.: 10/644,333

(22) Filed: Aug. 20, 2003

(65) Prior Publication Data

US 2004/0039011 A1    Feb. 26, 2004

Related U.S. Application Data

(63) Continuation of application No. 10/096,810, filed on Mar. 12, 2002, now abandoned.

(60) Provisional application No. 60/281,876, filed on Apr. 5, 2001.

(30) Foreign Application Priority Data

Mar. 13, 2001   (DE) .................................. 101 11 843

(51) Int. Cl.
   *A61K 31/4745*   (2006.01)
   *A61K 31/57*      (2006.01)
(52) U.S. Cl. ........................ 514/291; 514/171; 514/179
(58) Field of Classification Search .................. 514/291, 514/958, 54, 56, 393, 398, 630, 23, 557, 514/564, 642; 424/45, 400
See application file for complete search history.

(56) References Cited

U.S. PATENT DOCUMENTS

| | | | |
|---|---|---|---|
| 5,250,286 A * | 10/1993 | Skupin ............................. 424/45 |
| 5,610,163 A | 3/1997 | Banholzer et al. |
| 5,824,669 A * | 10/1998 | Garvey et al. ................. 514/174 |
| 5,948,792 A | 9/1999 | Tsuchiya et al. |
| 6,150,418 A * | 11/2000 | Hochrainer et al. .......... 514/630 |
| 6,197,762 B1 * | 3/2001 | Garvey et al. ................. 514/174 |
| 6,537,524 B1 * | 3/2003 | Hassan et al. .................... 424/45 |
| 6,653,313 B2 * | 11/2003 | Kawamura et al. ....... 514/253.04 |
| 6,919,069 B2 * | 7/2005 | Akehurst et al. ................ 424/45 |
| 2001/0008632 A1 * | 7/2001 | Freund et al. ................. 424/400 |
| 2002/0099023 A1 * | 7/2002 | Boucher, Jr. ..................... 514/23 |
| 2002/0111495 A1 * | 8/2002 | Magee et al. .................. 546/291 |
| 2002/0122773 A1 * | 9/2002 | Pairet et al. ...................... 424/45 |
| 2002/0193394 A1 * | 12/2002 | Disse .............................. 514/291 |

FOREIGN PATENT DOCUMENTS

| | | | |
|---|---|---|---|
| WO | WO 98/00119 | | 1/1998 |
| WO | WO 98/27959 | * | 7/1998 |
| WO | WO 99 66944 A | | 12/1999 |
| WO | WO 00/47200 | | 8/2000 |
| WO | WO 01/10427 A2 | | 2/2001 |
| WO | WO 01/12167 A2 | | 2/2001 |
| WO | WO 01/78739 A1 | | 10/2001 |

OTHER PUBLICATIONS

Definition of bronchitis and chronic bronchitis from On-line Medical dictionary, Database Google.com.*
Definition of bronchitis and chronic bronchitis from merriam-Webster (Medline plus) on-line dictionary, Database Google.com.*
F.P.V. Maesen, J.J. Smeets, T.J.H. Sledsens, F.D.M. Wald, and P.J.G. Cornelissen, Tiotropium bromide, a new long-acting antimuscarinic bronchodilator: a pharmacodynamic study in patients with chronic obstructive pulmonary disease (COPD), Eur. Respir J, 1995, 8, 1506-1513.*
P.M. O'Byrne and D.S.Postma, The Many Faces of Airway Inflammation, Am. j. Respir Crit. Care. Med. vol. 159, pp. s41-s66, 1999.*
Gerd J. Cropp, Effectiveness of bronchodilators in cystic fibrosis, The American Journal of Medicine, vol. 100, Supplement 1, Jan. 29, 1996, S19-S29.*
Peter J. Barnes, The Pharmacological Properties of Tiotropium, Chest, 117(2) February, 2000, 63S-66S.*
Littner, M. R. et al; "Long-Acting Bronchodilation with Once-Daily Dosing of Tiotropium (Spiriva) in Stable Chronic Obstructive Pulmonary Disease"; Am J Resp and Critical Care Med; Am Lung Assn,; 161(41) 2000; pp. 1136-1142; XP001148373.
Lasserson, T. et al; "Anticholinergic Therapy For Bronchiectasis"; Cochrane Database of Systematic Reviews; 4; 2001; XP008019810.
Rogers, D. F.; "Mucus pathophysiology in COPD: differences to asthma, and pharmacotherapy"; Monaldi Archives for Chest Disease, 55(4); 2000, pp. 324-332; XP008019816.
Witek T. J., JR: "Anticholinergic Bronchodilators." Respiratory Care Clinics of North America. United States Dec. 1999, Bd. 5, Nr. 4, Dec. 1999 pp. 521-536 XP008014468, ISSN: 1078-5337.
Wegner, Craig, Novel Mechanistic Targets for the Treatment of Sub-Acute and Chronic Bronchitis, Current Pharmaceutical Design, 2001, vol. 7, pp. 199-212, full text, especially p. 201.
Peter Barnes, Novel Approaches and Targets for Treatment of Chronic Obstructive Pulmonary Disease, American Journal of Respiratory and Critical Care Medicine, vol. 160(5), Nov. 1999, pp. S72-S79.
Leckie et al., Novel Therapy for COPD., Database CAPLUS, AN 2000:16639, abstract only, Expert Opinion on Investigational Drugs, 2000, vol. 9(1), pp. 3-23.
"bronchitis", The American Heritage Dictionary of the English Language, Foruth Edition 2000.
Barnes, Peter, Muscarinio receptor subtypes in airways, Database GOOGLE.com abstract alone, Euroconference, Apr. 1998.
Product information: Tiotropium Bromide (SPIRIVA TM), Database GOOGLE.com, Drugs of the future, 2000, vol. 25(7):693-699.
Petty, T., The Rising Epidemic COPD in Women, Database GOOGLE.com, 1999, vol. 2(12), pp. 942-953.

* cited by examiner

*Primary Examiner* — Michael G Hartley
*Assistant Examiner* — Jagadishwar Samala
(74) *Attorney, Agent, or Firm* — Michael P. Morris; Wendy A. Petka

(57) ABSTRACT

The invention relates to the use of (1α.2β,4β.5α.7β)-7-[(hydroxydi-2-thienylacetyl)oxy]-9,9-dimethyl-3-oxa-9-azoniatricyclo[3.3.1.0$^{2,4}$]nonane salts for preparing a pharmaceutical composition for the prevention and treatment of diseases associated with inflammation.

21 Claims, 3 Drawing Sheets

COMPOUNDS FOR TREATING INFLAMMATORY DISEASES

The invention relates to the use of $(1\alpha,2\beta,4\beta,5\alpha,7\beta)$-7-[(hydroxydi-2-thienylacetyl)oxy]-9,9-dimethyl-3-oxa-9-azoniatricyclo[3.3.1.0$^{2,4}$]nonane salts for preparing a pharmaceutical composition for the prevention and treatment of diseases associated with inflammation.

Antimuscarinics which are also often referred to in clinical practice as anticholinergics are firmly established in the treatment of diseases of the respiratory tract. For example, the administration of ipratropium bromide by inhalation (Atrovent®) as a bronchodilator is frequently a fixed part of the treatment for COPD, a term used hereinafter to refer to the related syndromes of chronic bronchitis, chronic obstructive bronchitis and pulmonary emphysema. Anticholinergics are also used to treat asthma on account of their bronchodilatory effect.

The compound $(1\alpha,2\beta,4\beta,5\alpha,7\beta)$-7-[(hydroxydi-2-thienylacetyl)oxy]-9,9-dimethyl-3-oxa-9-azoniatricyclo[3.3.1.0$^{2,4}$]nonane-bromide is known from European Patent Application EP 418 716 A1 and has the following chemical structure:

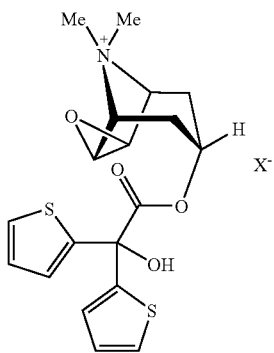

1 where X denotes bromide. The term tiotropium should be taken as being a reference to the free cation (1') within the scope of the present invention.

Tiotropium bromide, as well as other salts of tiotropium, are known as highly effective anticholinergic bronchodilators and can therefore provide therapeutic benefit in the treatment of asthma or COPD.

Tiotropium salts 1 are preferably administered by inhalation. Suitable inhalable powders packed into appropriate capsules (inhalettes) and administered using suitable powder inhalers may be used. Alternatively, they may be administered by the use of suitable inhalable aerosols. These also include powdered inhalable aerosols which contain, for example, HFA134a, HFA227 or mixtures thereof as propellant gas. The preparations may also be inhaled in the form of suitable solutions of the tiotropium salt 1.

Surprisingly, it has now been found that the antimuscarinically active tiotropium salts 1 can not only be used effectively as bronchodilators in diseases such as COPD for example, but are also characterised by an anti-inflammatory activity. This is due to the fact that the release of inflammatory mediators such as 15-HETE from epithelial cells such as histamine, leukotrienes and tryptase from mast cells, chemotactic activity (for neutrophilic granulocytes, eosinophilic granulocytes and macrophages) such as LTB4 and Interleukin 8 from alveolar macrophages is brought about or promoted by acetylcholine and inhibited by tiotropium. Surprisingly, it has been found that this potential, which can theoretically be attributed to all antimuscarinic active substances, comes into play only in conjunction with an active substance like tiotropium which dissociates itself from the receptor very slowly, as chemotactic and inflammatory activity has to be switched off permanently and not just intermittently in order to be biologically and clinically effective.

Figure 1:
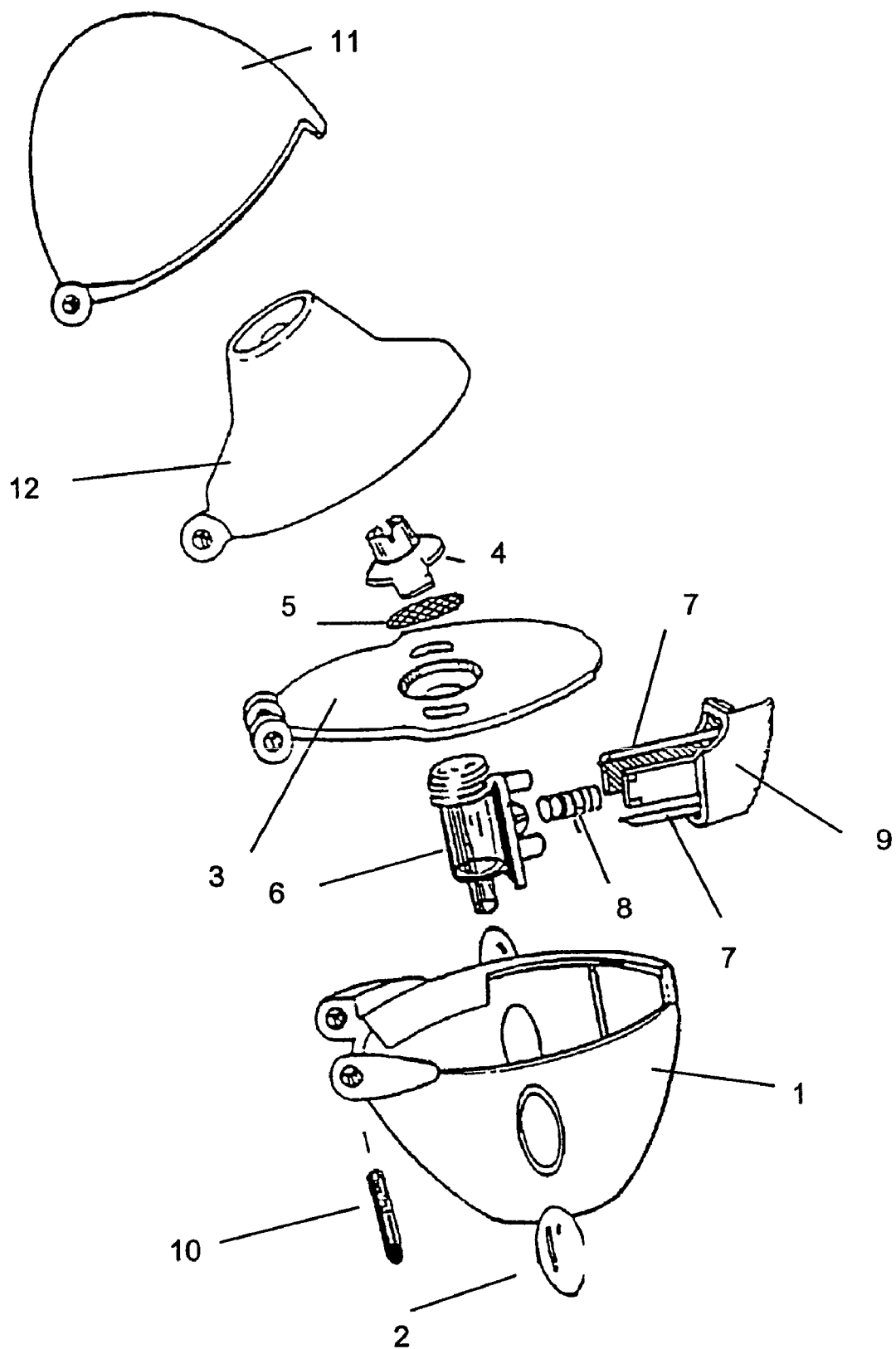
FIG. 1: An inhaler for the administration of the pharmaceutical combination according to the invention.
Figure 2A:
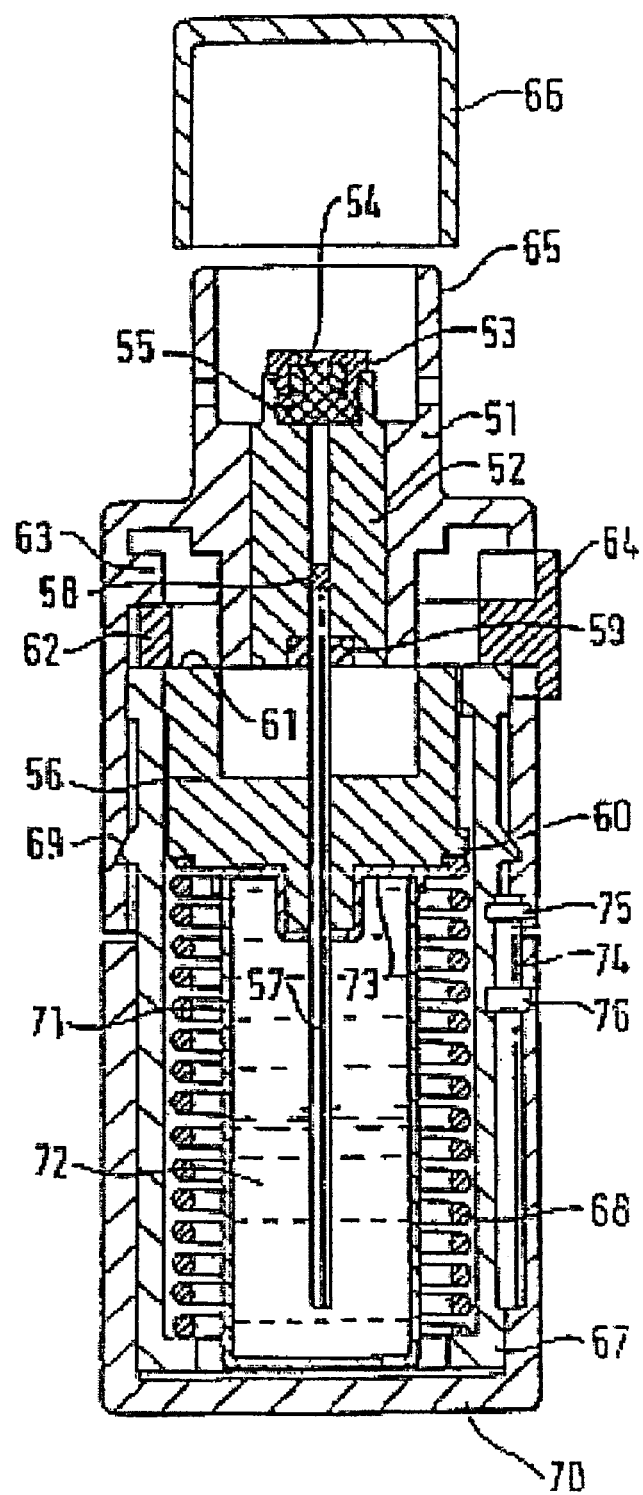
FIG. 2a: View of the longitudinal section through the atomizer with the spring biased.
Figure 2B:
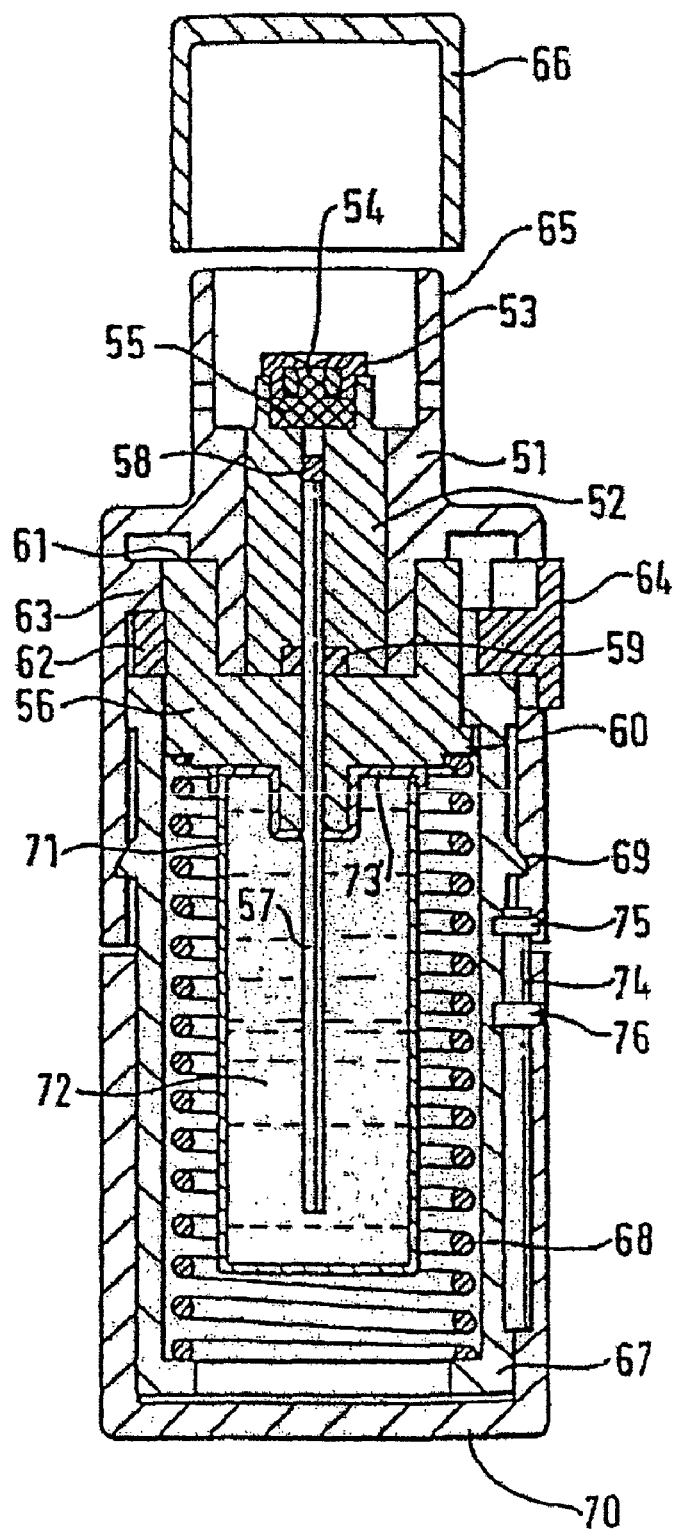
FIG. 2b: View of the longitudinal section through the atomizer with the spring relaxed.

The invention therefore relates to the use of tiotropium salts 1 for preparing a pharmaceutical composition for preventing or treating diseases associated with inflammation.

Preferably, the present invention relates to the use of tiotropium salts 1 for preparing a pharmaceutical composition for treating the inflammatory component in diseases of the upper and lower respiratory organs including the lungs, such as for example allergic or non-allergic rhinitis, chronic rhinitis, bronchiectasis, cystic fibrosis, asthma, COPD, idiopathic lung fibrosis, fibrosing alveolitis, skin diseases such as atopical dermatitis and urticaria as well as inflammatory bowel diseases.

Preferably, tiotropium salts 1 are used to treat inflammation in conjunction with other pulmonary diseases such as, for example, asthma and chronic (obstructive) bronchitis with and without emphysema, bronchiectasis, cystic fibrosis and fibrosing alveolitis.

By the tiotropium salts 1 which may be used within the scope of the present invention are meant the compounds which contain, in addition to tiotropium as counter-ion (anion), chloride, bromide, iodide, methanesulphonate, para-toluenesulphonate or methylsulphate. Within the scope of the present invention, the methanesulphonate, chloride, bromide and iodide are preferred of all the tiotropium salts, the methanesulphonate and bromide being of particular importance. Tiotropium bromide is of outstanding importance according to the invention.

In another aspect the present invention relates to pharmaceutical preparations for treating the abovementioned diseases. Without restricting the scope of the invention thereto, these may contain tiotropium 1' in amounts such that each individual dose contains 0.1-80 μg, preferably 0.5-60 μg, most preferably about 1-50 μg. For example, and without restricting the scope of the invention thereto, 2.5 μg, 5 μg, 10 μg, 18 μg, 20 μg, 36 μg or 40 μg of 1' may be administered per single dose.

If tiotropium bromide is used as the preferred tiotropium salt 1 according to the invention, the amounts of active substance 1' administered per single dose as specified hereinbefore by way of example correspond to the following amounts of 1 administered per single dose: 3 μg, 6 μg, 12 μg, 21.7 μg, 24.1 μg, 43.3 μg and 48.1 μg 1.

Use of tiotropium salts 1 according to the invention includes the use of the solvates and hydrates thus formed, preferably the hydrates, most preferably the monohydrates.

If for example tiotropium bromide monohydrate is used as the preferred tiotropium salt 1 according to the invention, the amounts of active substance 1' administered per single dose as specified hereinbefore by way of example correspond to the following amounts of 1 (monohydrate) administered per single dose: 3.1 µg, 6.2 µg, 12.5 µg, 22.5 µg, 25 µg, 45 µg and 50 µg.

The tiotropium salts 1 are preferably administered according to the invention by inhalation. For this purpose, the tiotropium salts 1 have to be prepared in inhalable forms. Inhalable preparations include inhalable powders, propellant-containing metering aerosols or propellant-free inhalable solutions. Inhalable powders according to the invention containing the tiotropium salts 1 optionally mixed with physiologically acceptable excipients. Within the scope of the present invention, the term propellant-free inhalable solutions also includes concentrates or sterile inhalable solutions ready for use. The formulations which may be used within the scope of the present invention are described in more detail in the next part of the specification.

A) Inhalable Powder:

The inhalable powders which may be used according to the invention may contain 1 either on its own or in admixture with suitable physiologically acceptable excipients.

If the tiotropium salts 1 are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrane), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 µm, preferably between 10 and 150 µm, most preferably between 15 and 80 µm. It may sometimes seem appropriate to add finer excipient fractions with an average particle size of 1 to 9 µm to the excipients mentioned above. These finer excipients are also selected from the group of possible excipients listed hereinbefore. Finally, in order to prepare the inhalable powders according to the invention, micronised active substance 1, preferably with an average particle size of 0.5 to 10 µm, more preferably from 1 to 6 µm, is added to the excipient mixture. Processes for producing the inhalable powders according to the invention by grinding and micronising and by finally mixing the ingredients together are known from the prior art.

Inhalable powders according to the invention which contain a physiologically acceptable excipient in addition to 1 may be administered, for example, by means of inhalers which deliver a single dose from a supply using a measuring chamber as described in U.S. Pat. No. 4,570,630A, or by other means as described in DE 36 25 685 A. The inhalable powders according to the invention which contain 1 optionally in conjunction with a physiologically acceptable excipient may be administered for example using an inhaler known by the name Turbuhaler® or using inhalers as disclosed for example in EP 237507 A. Preferably, the inhalable powders according to the invention which contain physiologically acceptable excipient in addition to 1 are packed into capsules (to produce so-called inhalettes) which are used in inhalers as described, for example, in WO 94/28958.

A particularly preferred inhaler for administering the pharmaceutical combination according to the invention in inhalettes is shown in FIG. 1.

This inhaler (Handyhaler) for inhaling powdered pharmaceutical compositions from capsules is characterised by a housing 1 containing two windows 2, a deck 3 in which there are air inlet ports and which is provided with a screen 5 secured via a screen housing 4, an inhalation chamber 6 connected to the deck 3 on which there is a push button 8 [sic] provided with two sharpened pins 7 and movable counter to a spring 8, and a mouthpiece 12 which is connected to the housing 1, the deck 3 and a cover 11 via a spindle 10 to enable it to be flipped open or shut.

If the inhalable powders according to the invention are packed into capsules (inhalers) for the preferred use described above, the quantities packed into each capsule should be 1 to 30 mg, preferably 3 to 20 mg, more particularly 5 to 10 mg of inhalable powder per capsule. These capsules contain, according to the invention, either together or separately, the doses of 1' mentioned hereinbefore for each single dose.

B) Propellant Gas-Driven Inhalation Aerosols:

Inhalation aerosols containing propellant gas which may be used according to the invention may contain substances 1 dissolved in the propellant gas or in dispersed form. The propellant gases which may be used to prepare the inhalation aerosols are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof.

The propellant-driven inhalation aerosols which may be used according to the invention may also contain other ingredients such as co-solvents, stabilisers, surfactants, antioxidants, lubricants and pH adjusters. All these ingredients are known in the art.

The propellant-driven inhalation aerosols which may be used according to the invention may contain up to 5 wt. % of active substance 1. The propellant-driven inhalation aerosols which may be used according to the invention contain, for example, 0.002 to 5 wt. %, 0.01 to 3 wt. %, 0.015 to 2 wt. % of active substance 1.

If the active substances 1 are present in dispersed form, the particles of active substance preferably have an average particle size of up to 10 µm, preferably from 0.1 to 5 µm, more preferably from 1 to 5 µm.

The propellant-driven inhalation aerosols according to the invention which may be used according to the invention may be administered using inhalers known in the art (MDIs=metered dose inhalers). Accordingly, in another aspect, the present invention relates to the use of 1 according to the invention to prepare pharmaceutical compositions in the form of propellant-driven aerosols as hereinbefore described combined with one or more inhalers suitable for administering these aerosols.

In addition, the present invention relates to the use of 1 according to the invention to prepare cartridges which when fitted with a suitable valve can be used in a suitable inhaler and which contain one of the above-mentioned propellant gas-containing inhalation aerosols according to the invention. Suitable cartridges and methods of filling these cartridges with the inhalable aerosols containing propellant gas according to the invention are known from the prior art.

C) Propellant-Free Inhalable Solutions:

It is particularly preferred to use the tiotropium salts 1 according to the invention to prepare propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is up to 70 percent by volume, more particularly up to 60 percent by volume and most preferably up to 30 percent by volume. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

According to the invention, the addition of editic acid (EDTA) or one of the known salts thereof, sodium edetate, as stabiliser or complexing agent is unnecessary in the present formulation. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred.

Co-solvents and/or other excipients may be added to the propellant-free inhalable solutions which may be used according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the tiotropium salts 1, only benzalkonium chloride and sodium edetate. In another preferred embodiment, no sodium edetate is present.

The propellant-free inhalable solutions which may be used within the scope of the invention are administered in particular using inhalers of the kind which are capable of nebulising a small amount of a liquid formulation in the therapeutic dose within a few seconds to produce an aerosol suitable for therapeutic inhalation. Within the scope of the present invention, preferred inhalers are those in which a quantity of less than 100 µL, preferably less than 50 µL, more preferably between 10 and 30 µL of active substance solution can be nebulised in preferably one spray action to form an aerosol with an average particle size of less than 20 µm, preferably less than 10 µm, in such a way that the inhalable part of the aerosol corresponds to the therapeutically effective quantity.

An apparatus of this kind for propellant-free delivery of a metered quantity of a liquid pharmaceutical composition for inhalation is described for example in International Patent Application WO 91/14468 and also in WO 97/12687 (cf. in particular FIGS. 6a and 6b). The nebulisers (devices) described therein are also known by the name Respimat®.

This nebuliser (Respimat®) can advantageously be used to produce the inhalable aerosols according to the invention containing the tiotropium salts 1. Because of its cylindrical shape and handy size of less than 9 to 15 cm long and 2 to 4 cm wide, this device can be carried at all times by the patient. The nebuliser sprays a defined volume of pharmaceutical formulation using high pressures through small nozzles so as to produce inhalable aerosols.

The preferred atomiser essentially consists of an upper housing part, a pump housing, a nozzle, a locking mechanism, a spring housing, a spring and a storage container, characterised by a pump housing which is secured in the upper housing part and which comprises at one end a nozzle body with the nozzle or nozzle arrangement, a hollow plunger with valve body, a power takeoff flange in which the hollow plunger is secured and which is located in the upper housing part, a locking mechanism situated in the upper housing part, a spring housing with the spring contained therein, which is rotatably mounted on the upper housing part by means of a rotary bearing, a lower housing part which is fitted onto the spring housing in the axial direction.

The hollow plunger with valve body corresponds to a device disclosed in WO 97/12687. It projects partially into the cylinder of the pump housing and is axially movable within the cylinder. Reference is made in particular to FIGS. 1 to 4, especially FIG. 3, and the relevant parts of the description. The hollow plunger with valve body exerts a pressure of 5 to 60 Mpa (about 50 to 600 bar), preferably 10 to 60 Mpa (about 100 to 600 bar) on the fluid, the measured amount of active substance solution, at its high pressure end at the moment when the spring is actuated. Volumes of 10 to 50 microliters are preferred, while volumes of 10 to 20 microliters are particularly preferred and a volume of 15 microliters per spray is most particularly preferred.

The valve body is preferably mounted at the end of the hollow plunger facing the valve body.

The nozzle in the nozzle body is preferably microstructured, i.e. produced by microtechnology. Microstructured valve bodies are disclosed for example in WO-94/07607; reference is hereby made to the contents of this specification, particularly FIG. 1 therein and the associated description.

The valve body consists for example of two sheets of glass and/or silicon firmly joined together, at least one of which has one or more microstructured channels which connect the nozzle inlet end to the nozzle outlet end. At the nozzle outlet end there is at least one round or non-round opening 2 to 10 microns deep and 5 to 15 microns wide, the depth preferably being 4.5 to 6.5 microns while the length is preferably 7 to 9 microns.

In the case of a plurality of nozzle openings, preferably two, the directions of spraying of the nozzles in the nozzle body may extend parallel to one another or may be inclined relative to one another in the direction of the nozzle opening. In a nozzle body with at least two nozzle openings at the outlet end the directions of spraying may be at an angle of 20 to 160° to one another, preferably 60 to 150°, most preferably 80 to 100°. The nozzle openings are preferably arranged at a spacing of 10 to 200 microns, more preferably at a spacing of 10 to 100 microns, most preferably 30 to 70 microns. Spacings of 50 microns are most preferred. The directions of spraying will therefore meet in the vicinity of the nozzle openings.

The liquid pharmaceutical preparation strikes the nozzle body with an entry pressure of up to 600 bar, preferably 200 to 300 bar, and is atomised into an inhalable aerosol through the nozzle openings. The preferred particle or droplet sizes of the aerosol are up to 20 microns, preferably 3 to 10 microns.

The locking mechanism contains a spring, preferably a cylindrical helical compression spring, as a store for the mechanical energy. The spring acts on the power takeoff flange as an actuating member the movement of which is determined by the position of a locking member. The travel of the power takeoff flange is precisely limited by an upper and lower stop. The spring is preferably biased, via a power step-up gear, e.g. a helical thrust gear, by an external torque which is produced when the upper housing part is rotated counter to the spring housing in the lower housing part. In this case, the upper housing part and the power takeoff flange have a single or multiple V-shaped gear.

The locking member with engaging locking surfaces is arranged in a ring around the power takeoff flange. It consists, for example, of a ring of plastic or metal which is inherently radially elastically deformable. The ring is arranged in a plane at right angles to the atomiser axis. After the biasing of the spring, the locking surfaces of the locking member move into the path of the power takeoff flange and prevent the spring from relaxing. The locking member is actuated by means of a button. The actuating button is connected or coupled to the locking member. In order to actuate the locking mechanism, the actuating button is moved parallel to the annular plane, preferably into the atomiser; this causes the deformable ring to deform in the annual plane. Details of the construction of the locking mechanism are given in WO 97/20590.

The lower housing part is pushed axially over the spring housing and covers the mounting, the drive of the spindle and the storage container for the fluid.

When the atomiser is actuated the upper housing part is rotated relative to the lower housing part, the lower housing part taking the spring housing with it. The spring is thereby compressed and biased by means of the helical thrust gear and the locking mechanism engages automatically. The angle of rotation is preferably a whole-number fraction of 360 degrees, e.g. 180 degrees. At the same time as the spring is biased, the power takeoff part in the upper housing part is moved along by a given distance, the hollow plunger is withdrawn inside the cylinder in the pump housing, as a result of which some of the fluid is sucked out of the storage container and into the high pressure chamber in front of the nozzle.

If desired, a number of exchangeable storage containers which contain the fluid to be atomised may be pushed into the atomiser one after another and used in succession. The storage container contains the aqueous aerosol preparation according to the invention.

The atomising process is initiated by pressing gently on the actuating button. As a result, the locking mechanism opens up the path for the power takeoff member. The biased spring pushes the plunger into the cylinder of the pump housing. The fluid leaves the nozzle of the atomiser in atomised form.

Further details of construction are disclosed in PCT Applications WO 97/12683 and WO 97/20590, to which reference is hereby made.

The components of the atomiser (nebuliser) are made of a material which is suitable for its purpose. The housing of the atomiser and—if its operation permits—other parts as well are preferably made of plastics, e.g. by injection moulding. For medicinal purposes, physiologically safe materials are used.

FIGS. 2*a/b* attached to this patent application, which are identical to FIGS. 6*a/b* of WO 97/12687, show the nebuliser (Respimat®) which can advantageously be used for inhaling the aqueous aerosol preparations according to the invention.

FIG. 2*a* shows a longitudinal section through the atomiser with the spring biased while FIG. 2*b* shows a longitudinal section through the atomiser with the spring relaxed.

The upper housing part (51) contains the pump housing (52) on the end of which is mounted the holder (53) for the atomiser nozzle. In the holder is the nozzle body (54) and a filter (55). The hollow plunger (57) fixed in the power takeoff flange (56) of the locking mechanism projects partially into the cylinder of the pump housing. At its end the hollow plunger carries the valve body (58). The hollow plunger is sealed off by means of the seal (59). Inside the upper housing part is the stop (60) on which the power takeoff flange abuts when the spring is relaxed. On the power takeoff flange is the stop (61) on which the power takeoff flange abuts when the spring is biased. After the biasing of the spring the locking member (62) moves between the stop (61) and a support (63) in the upper housing part. The actuating button (64) is connected to the locking member. The upper housing part ends in the mouthpiece (65) and is sealed off by means of the protective cover (66) which can be placed thereon.

The spring housing (67) with compression spring (68) is rotatably mounted on the upper housing part by means of the snap-in lugs (69) and rotary bearing. The lower housing part (70) is pushed over the spring housing. Inside the spring housing is the exchangeable storage container (71) for the fluid (72) which is to be atomised. The storage container is sealed off by the stopper (73) through which the hollow plunger projects into the storage container and is immersed at its end in the fluid (supply of active substance solution).

The spindle (74) for the mechanical counter is mounted in the covering of the spring housing. At the end of the spindle facing the upper housing part is the drive pinion (75). The slider (76) sits on the spindle.

The nebuliser described above is suitable for nebulising the aerosol preparations which may be used according to the invention to produce an aerosol suitable for inhalation.

If the propellant-free inhalable solutions which may be used according to the invention are nebulised using the method described above (Respimat®) the quantity delivered should correspond to a defined quantity with a tolerance of not more than 25%, preferably 20% of this amount in at least 97%, preferably at least 98% of all operations of the inhaler (spray actuations). Preferably, between 5 and 30 mg of formulation, most preferably between 5 and 20 mg of formulation are delivered as a defined mass on each actuation.

However, the propellant-free inhalable solutions which may be used according to the invention may also be nebulised by means of inhalers other than those described above, e.g. jet stream inhalers or other stationary nebulisers.

Accordingly, in a further aspect, the invention relates to the use according to the invention of tiotropium salts 1 for preparing a pharmaceutical formulation in the form of propellant-free inhalable solutions or suspensions as described above combined with a device suitable for administering these formulations, preferably in conjunction with the Respimat®. Preferably, the invention relates to the use according to the invention of compounds 1 for preparing propellant-free inhalable solutions or suspensions characterised in that they contain 1 in conjunction with the device known by the name Respimat®. In addition, the present invention relates to the use according to the invention of the above-mentioned devices for inhalation, preferably the Respimat®, characterised in that they contain the propellant-free inhalable solutions or suspensions according to the invention as described hereinbefore.

The propellant-free inhalable solutions or suspensions which may be used within the scope of the invention may take the form of concentrates or sterile inhalable solutions or suspensions ready for use, as well as the above-mentioned solutions and suspensions designed for use in a Respimat®. Formulations ready for use may be produced from the concentrates, for example, by the addition of isotonic saline solutions. Sterile formulations ready for use may be administered using energy-operated fixed or portable nebulisers which produce inhalable aerosols by means of ultrasound or compressed air by the Venturi principle or other principles.

Accordingly, in another aspect, the present invention relates to the use according to the invention of 1 in the form of propellant-free inhalable solutions or suspensions as described hereinbefore which take the form of concentrates or sterile formulations ready for use, combined with a device suitable for administering these solutions, characterised in that the device is an energy-operated free-standing or portable nebuliser which produces inhalable aerosols by means of ultrasound or compressed air by the Venturi principle or other methods.

The Examples which follow serve to illustrate the present invention in more detail without restricting the scope of the invention to the following embodiments by way of example.

Starting Materials

Tiotropium Bromide:

The tiotropium bromide used in the following formulation examples may be obtained as described in European Patent Application EP 418 716 A1.

In order to prepare the inhalable powders according to the invention, crystalline tiotropium bromide monohydrate may also be used. This crystalline tiotropium bromide monohydrate may be obtained by the method described below.

15.0 kg of tiotropium bromide are placed in 25.7 kg of water in a suitable reaction vessel. The mixture is heated to 80-90° C. and stirred at constant temperature until a clear solution is formed. Activated charcoal (0.8 kg) moistened with water is suspended in 4.4 kg of water, this mixture is added to the solution containing the tiotropium bromide and the resulting mixture is rinsed with 4.3 kg of water. The mixture thus obtained is stirred for at least 15 minutes at 80-90° C. and then filtered through a heated filter into an apparatus preheated to an external temperature of 70° C. The filter is rinsed with 8.6 kg of water. The contents of the apparatus are cooled at 3-5° C. for every 20 minutes to a temperature of 20-25° C. The apparatus is cooled further to 10-15° C. using cold water and crystallisation is completed by stirring for at least another hour. The crystals are isolated using a suction filter dryer, the crystal slurry isolated is washed with 9 liters of cold water (10-15° C.) and cold acetone (10-15° C.). The crystals obtained are dried at 25° C. in a nitrogen current over a period of 2 hours.

Yield: 13.4 kg of tiotropium bromide monohydrate (86% of theory).

The crystalline tiotropium bromide monohydrate thus obtained is micronised by known methods in order to prepare the active substance in the form of the average particle size corresponding to the specifications according to the invention.

EXAMPLES OF FORMULATIONS

| A) Inhalable powders: | |
|---|---|
| Ingredients | μg per capsule |
| 1) | |
| tiotropium bromide | 10.8 |
| lactose | 4989.2 |
| Total | 5000 |
| 2) | |
| titropium bromide | 21.7 |
| lactose | 4978.3 |
| Total | 5000 |
| 3) | |
| tiotropium bromide × $H_2O$ | 22.5 |
| lactose | 4977.5 |
| Total | 5000 |

| B) Inhalable aerosols containing propellant gas: | |
|---|---|
| Ingredients | wt. % |
| 1) Suspension aerosol: | |
| tiotropium bromide | 0.015 |
| soya lecithin | 0.2 |
| TG 134a:TG227 = 2:3 | ad 100 |
| 2) Suspension aerosol: | |
| tiotropium bromide | 0.029 |
| absolute ethanol | 0.5 |
| isopropyl myristate | 0.1 |
| TG 227 | ad 100 |
| 3) Solution aerosol: | |
| tiotropium bromide | 0.042 |
| absolute ethanol | 30 |
| purified water | 1.5 |
| anhydrous citric acid | 0.002 |
| TG 134a | ad 100 |

-continued

| C) Propellant-free inhalable solutions: | |
|---|---|
| Ingredients | mg/100 mL |

1) Solution for use in the Respimat ®:

| | |
|---|---|
| tiotropium bromide | 148.5 |
| benzalkonium chloride | 10 |
| sodium edetate | 10 |
| hydrochloric acid (aq) | ad pH 2.9 |
| water | ad 100 mL |

Using the solution in the Respimat leads to a dosage of 10 μg per dose of 1.

2) Solution for use in the Respimat ®:

| | |
|---|---|
| tiotropium bromide | 148.5 |
| benzalkonium chloride | 10 |
| hydrochloric acid (aq) | ad pH 2.9 |
| water | ad 100 mL |

Using the solution in the Respimat leads to a dosage of 10 μg per dose of 1.

3) Solution for use in the Respimat ®:

| | |
|---|---|
| tiotropium bromide | 297.1 |
| benzalkonium chloride | 10 |
| sodium edetate | 10 |
| hydrochloric acid (aq) | ad pH 2.9 |
| water | ad 100 mL |

Using the solution in the Respimat leads to a dosage of 20 μg per dose of 1 and 25 μg/dose of 2.

4) Solution for use in the Respimat ®:

| | |
|---|---|
| tiotropium bromide | 297.1 |
| benzalkonium chloride | 10 |
| hydrochloric acid (aq) | ad pH 2.9 |
| water | ad 100 mL |

Using the solution in the Respimat leads to a dosage of 20 μg per dose of 1.

5) Solution for use in the Respimat ®:

| | |
|---|---|
| tiotropium bromide | 148.5 |
| benzalkonium chloride | 8 |
| sodium edetate | 50 |
| hydrochloric acid (aq) | ad pH 2.5 |
| water | ad 100 mL |

Using the solution in the Respimat leads to a dosage of 10 μg per dose of 1.

6) Solution for use in the Respimat ®:

| | |
|---|---|
| tiotropium bromide | 1.5 |
| benzalkonium chloride | 8 |
| sodium edetate | 10 |
| hydrochloric acid (aq) | ad pH 2.5 |
| water | ad 100 mL |

Using the solution in the Respimat leads to a dosage of 0.1 μg per dose of 1.

7) Solution for use in the Respimat ®:

| | |
|---|---|
| tiotropium bromide | 14,9 |
| benzalkonium chloride | 10 |
| sodium edetate | 50 |
| hydrochloric acid (aq) | ad pH 3.5 |
| water | ad 100 mL |

Using the solution in the Respimat leads to a dosage of 1 μg per dose of 1.

8) Concentrated solution:

| | |
|---|---|
| tiotropium bromide | 1486.1 |
| benzalkonium chloride | 20 |
| sodium edetate | 100 |
| hydrochloric acid (aq) | ad pH 3.5 |
| water | ad 100 mL |

What is claimed is:

1. A method for treating an inflammatory component of cystic fibrosis, which method comprises administering, via inhalation, a formulation wherein the active substance consists of a therapeutically effective amount of a salt of tiotropium, and, optionally, physiologically acceptable excipients, and wherein the salt of tiotropium provides an anti-inflammatory activity.

2. The method as recited in claim 1 wherein the tiotropium salt has an anion selected from chloride, bromide, iodide, methanesulphonate, paratoluenesulphonate and methylsulphate.

3. The method as recited in claim 2 wherein the anion of the tiotropium salt is methanesulphonate, chloride, bromide or iodide.

4. The method as recited in claim 3 wherein the anion of the tiotropium salt is methanesulphonate or bromide.

5. The method as recited in claim 3 wherein the anion of the tiotropium salt is bromide.

6. The method of claim 1, wherein the salt of tiotropium is administered via inhalation in a formulation selected from powders for inhalation, metered-dose aerosols containing propellant gas and propellant-gas-free inhalable solutions.

7. The method of claim 6, wherein the formulation is an inhalable powder which contains the tiotropium salt in admixture with a suitable physiologically acceptable excipient selected from monosaccharides, disaccharides, oligo- and polysaccharides, polyalcohols, salts, and mixtures thereof.

8. The method of claim 6, wherein the formulation is an inhalable aerosol containing a propellant gas, which contains the tiotropium salt in dissolved or dispersed form.

9. The method of claim 8, wherein the propellant gas is a hydrocarbon or halohydrocarbon gas.

10. The method of claim 8, wherein the propellant gas is n-butane, isobutane, or a fluorinated methane, ethane, propane, butane, cyclopropane or cyclobutane.

11. The method of claim 8, wherein the propellant gas is TG134a, TG227 or a mixture thereof.

12. The method of claim 8, wherein the inhalable aerosol further comprises one or more other ingredients selected from co-solvents, stabilizers, surfactants, antioxidants, lubricants and pH adjusters.

13. The method of claim 6, wherein the formulation is a propellant-free inhalable solution which further comprises a solvent selected from water, ethanol or a mixture of water and ethanol.

14. The method of claim 13, wherein the pH of the propellant-free inhalable solution is 2-7.

15. The method of claim 13, wherein the propellant-free inhalable solution further comprises a co-solvent which contains hydroxyl groups or other polar groups.

16. The method of claim 15, wherein the cosolvent is an alcohol or glycol.

17. The method of claim 15, wherein the propellant-free inhalable solution further comprises at least one surfactant, stabilizer, complexing agent, antioxidant, preservative, flavoring, pharmacologically acceptable salt or vitamin.

18. The method of claim 13, wherein the propellant-free inhalable solution contains only benzalkonium chloride and sodium edetate in addition to the active substance and the solvent.

19. The method of claim 13, wherein the propellant-free inhalable solution is a concentrate or a sterile inhalable solution ready for use.

20. The method of claim 6, wherein the formulation further comprises, as complexing agent, editic acid or a salt of editic acid.

21. The method of claim 6, wherein the formulation further comprises, as complexing agent, sodium edetate.

* * * * *